United States Patent [19]

Baumoel

[11] Patent Number: 5,548,530

[45] Date of Patent: Aug. 20, 1996

[54] HIGH-PRECISION LEAK DETECTOR AND LOCATOR

[76] Inventor: Joseph Baumoel, c/o Controlotron Corporation, 155 Plant Ave., Hauppauge, N.Y. 11788

[21] Appl. No.: 427,411

[22] Filed: Apr. 24, 1995

[51] Int. Cl.⁶ ..................................... G01F 1/66
[52] U.S. Cl. ........................ 364/509; 73/40.5 A
[58] Field of Search ............... 364/509 C, 510, 364/507, 558, 565, 569; 73/40.5 R, 40.5 A, 49.1, 49.5, 49.2, 40.7, 597, 598, 861.78, 861.31; 340/605; 367/99, 100, 125; 376/252

[56] References Cited

U.S. PATENT DOCUMENTS

| | | | |
|---|---|---|---|
| 3,851,521 | 12/1974 | Ottenstein | 73/40.5 R |
| 3,869,915 | 3/1975 | Baumoel | 73/861.28 |
| 3,903,729 | 9/1995 | Covington | 73/40.5 R |
| 3,987,662 | 10/1976 | Horn et al. | 73/40.5 R |
| 3,987,674 | 10/1976 | Baumoel | 73/597 |
| 4,232,548 | 11/1980 | Baumoel | 73/597 |
| 4,327,576 | 5/1982 | Dickey et al. | 73/40.5 A |
| 4,435,974 | 3/1984 | Fuchs et al. | 73/40.5 A |
| 5,058,419 | 10/1991 | Nordstrom et al. | 73/40.5 A |

Primary Examiner—James Trammell
Attorney, Agent, or Firm—Ostrolenk, Faber, Gerb & Soffen, LLP

[57] ABSTRACT

A method for detecting the presence of a leak in a segment of a pipeline. The method includes providing a site station having an ultra-sonic transducer assembly at the beginning and end of the pipeline segment, each assembly having two pairs of ultrasonic transducers for determining the sonic propagation velocity $V_s$ of ultrasonic energy emitted by the transducers through fluid in the pipeline. Each pair of ultrasonic transducers is displaced along the pipeline by a preset distance and each defines an ultrasonic energy flow path. The value of $V_s$ for each ultrasonic energy flow path through the fluid in the pipeline is determined at each site station at predetermined time intervals. Values $\Delta V_s$ defined as the difference between sequential values of $V_s$ at the predetermined time intervals for each flow path at each site station are formed. The $\Delta V_s$ values for each flow path are stored in a memory having a predetermined number of memory cells, where a value of $\Delta V_s$ is stored in each cell. A determination is made if there is a correlation in the stored values of $\Delta V_s$ for each flow path. If there is a correlation between the $\Delta V_s$ values for each path, a discrimination is performed between a correlation caused by zero values of $\Delta V_s$ stored in the memory for each path and a correlation of $\Delta V_s$ values reflecting that a transient in the fluid in the pipeline has arrived at each site station. Then a determination is made whether the correlation corresponds to a leak.

27 Claims, 4 Drawing Sheets

HIGH-PRECISION LEAK DETECTOR AND LOCATOR

BACKGROUND OF THE INVENTION

The present invention relates to a leak detector system for pipelines, and in particular, to a non-intrusive high-precision ultra-sonic leak detector system for pipelines. Even more particularly, the present invention relates to improvements in the Controlotron Model 1010 and version 3 990LD and 1010LD leak detection systems.

The Controlotron version 3 990 ultra-sonic flow meter is known. In this system, non-intrusive ultrasonic transducer clamp-on flow meters are employed to determine sonic propagation velocity through fluid in the pipe and other parameters. In so doing, a number of these flow meters can be employed along the length of a pipeline to determine if a leak exists.

SUMMARY OF THE INVENTION

It is an object of the present invention to adapt the known flow meter technology to identify the development of even very minute, for example, millimeter size leaks in a pipeline, e.g., a petroleum pipeline and compute the location of the leak within several meters of its actual location in a segment between two site stations of the overall leak detection system.

The principle by which such an event, a leak, can be determined and its location identified remotely, is by its effect on the pressure of the pipeline, and the effect of the pressure change on liquid density, which effects the sonic propagation velocity $V_s$ of the liquid. Detection of this change in $V_s$ is the means by which the pressure change is detected, and is done in such a way as to detect only those changes that are associated with a sudden pipeline opening in the pipeline segment being monitored, thereby discriminating against pressure changes originating elsewhere in the pipeline and also against slow changes in pressure and $V_s$ not associated with development of a leak.

Accordingly, it is an object of the present invention to provide a leak detection system for a pipeline which can determine the occurrence of leaks, including millimeter size leaks, for example, and preferably identify the location of the leak within several meters of its actual location, which should be clear, is more than enough accuracy than necessary for such a task.

It is furthermore an object of the present invention to provide an improvement to the known nonintrusive leak detection systems, but which can also be employed with intrusive systems.

It is furthermore an object of the present invention to provide a leak detection system which can detect only those changes that are associated with a sudden pipeline opening, i.e., a leak in the pipeline segment being monitored, and which can discriminate against pressure changes originating elsewhere in the pipeline and also against pressure changes not due to the development of a leak.

The above and other objects of the invention are achieved by a method for detecting the presence of a leak in a segment of a pipeline comprising: providing a site station comprising an ultra-sonic transducer assembly at the beginning and end of the pipeline segment, each said assembly having two pairs of ultrasonic transducers for determining the sonic propagation velocity $V_s$ of ultrasonic energy emitted by the transducers through fluid in the pipeline, each pair of ultrasonic transducers being displaced along the pipeline by a preset distance and each defining an ultrasonic energy flow path; determining the value of $V_s$ for each ultrasonic energy flow path through the fluid in the pipeline at each site station at predetermined time intervals; forming values $\Delta V_s$ defined as the difference between sequential values of $V_s$ at said predetermined time intervals for each flow path at each site station; storing said $\Delta V_s$ values for each flow path in a memory having a predetermined number of memory cells, where a value of $\Delta V_s$ is stored in each cell; determining if there is a correlation in the stored values of $\Delta V_s$ for each flow path; discriminating, if there is a correlation between the $\Delta V_s$ values for each path, between a correlation caused by zero values of $\Delta V_s$ stored in the memory for each path and a correlation of $\Delta V_s$ values reflecting that a transient in the fluid in the pipeline has arrived at each site station; determining, if there is a correlation wherein the $\Delta V_s$ values reflect that a transient has arrived at each site station, whether the correlation corresponds to a leak in the segment, and if so, indicating that a leak has occurred.

Preferably, the invention also indicates the location of the leak in the segment by triangulation between the two site stations at the two ends of the pipeline segment.

In order to discriminate between leaks and other disturbances, the number of cells in the memory is preferably such that substantially all $\Delta V_s$ values from a transient caused by a leak will be stored in the memory and substantially all $\Delta V_s$ values from transients not caused by leaks will not be stored in the memory because such transients not resulting from leaks are too slow to result in substantially all the $\Delta V_s$ values being stored in the memory.

Preferably, the step of discriminating comprises generating a correlation factor which indicates the relative strength and arrival time of a transient pulse as reflected in the $\Delta V_s$ values for each path in the memory, and using the correlation factor to determine whether there is a leak in the pipeline or some other condition which is not a leak.

The objects of the invention are also achieved by an apparatus comprising two site stations each having an ultrasonic transducer assembly provided respectively at the beginning and end of the pipeline segment, each said assembly having two pairs of ultrasonic transducers for determining the sonic propagation velocity $V_s$ of ultrasonic energy emitted by the transducers through fluid in the pipeline, each pair of ultrasonic transducers being displaced along the pipeline by a preset distance and each defining an ultrasonic energy flow path; a computer for determining the value of $V_s$ for each ultrasonic energy flow path through the fluid in the pipeline at each site station at predetermined time intervals; the computer further forming values $\Delta V_s$ defined as the difference between sequential values of $V_s$ at said predetermined time intervals for each flow path at each site station; a memory wherein said $\Delta V_s$ values are stored for each flow path having a predetermined number of memory cells, where a value of $V_s$ is stored in each cell; the computer determining if there is a correlation in the stored values of $\Delta V_s$ for each flow path and discriminating, if there is a correlation between the $\Delta V_s$ values for each path, between a correlation caused by zero values of $\Delta V_s$ stored in the memory for each path and a correlation of $\Delta V_s$ values reflecting that a transient in the fluid in the pipeline has arrived at each site station; and the computer further determining, if there is a correlation wherein the $\Delta V_s$ values reflect that a transient has arrived at each site station, whether the correlation corresponds to a leak in the segment, and if so, indicating that a leak has occurred.

Preferably, the invention also indicates the location of the leak in the segment by triangulation of the transient arrival time between the two site stations at the two ends of the pipeline segment.

Other objects, features and advantages of the present invention will be apparent from the detailed description which follows.

BRIEF DESCRIPTION OF THE DRAWING(S)

The invention will now be described in greater detail in the following detailed description with reference to the drawings in which.

DETAILED DESCRIPTION OF EMBODIMENTS OF THE INVENTION

Figure 1:
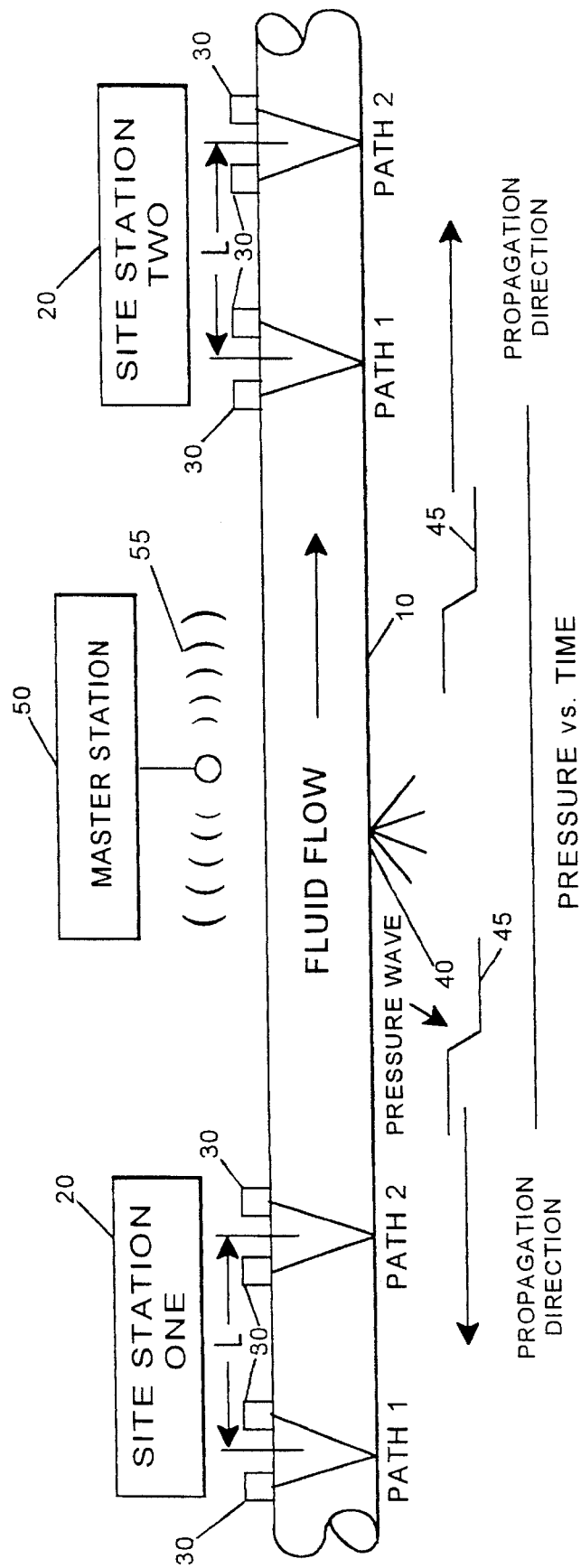
FIG. 1 is a schematic diagram of a pipeline showing one segment of the pipeline and two site stations on either side of the pipeline segment as well as a master station which polls the site stations.

With reference now to the drawings, the system can best be understood with reference to FIG. 1. This shows a pipeline segment 10 with a high-precision leak locator site station 20 (HPLL) at each end of the segment. Each site station 20 consists of one HPLL computer and two pairs of clamp-on, or as the case may be, wetted (intrusive), transit time transducers 30, of essentially identical structure to a dual-path system 990 site station manufactured by Controlotron Corporation of Hauppauge, N.Y. and already well defined in the literature. The two pairs of transducers establish two paths at each site station, PATH1 and PATH2. Such site stations are capable of measuring both flow rate and sonic propagation property $V_s$. In this case, the principal measurement of interest is that of $\Delta V_s$. As indicated, the present invention is applicable to both clamp-on non-intrusive transit time transducers as well as wetted or intrusive transit time transducers, which determine flow and $V_s$ based upon the transit time of ultrasonic energy through the fluid in the pipeline.

Depending on the diameter of the pipe, the $V_s$ of the liquid currently in the pipe, and the choice as between direct or reflect mount of the transducers (reflect mount shown in FIG. 1), the transit time of the ultrasonic pulse from one transducer to the other is of the order of magnitude of from tens of microseconds, to at most, several milliseconds. As such, it is reasonable to assume, for description purposes, that the site station 20 computer will generate one $V_s$ interrogation pulse every millisecond permitting interrogation at a frequency of about 1000 Hz. Since for any installation, the location of the transducers will be known, it is a simple matter for the computer to determine the value of $V_s$ from the measured transit time of the pulse over the path between the two transducers. This principle is well-known in the art. See for example, U.S. Pat. Nos. 3,869,915; 3,987,674; and 4,232,548. The same measurement can be made for each path, PATH1 and PATH2, either simultaneously or sequentially.

Note that the two paths will be displaced along the pipeline by a known distance L, as may be deemed beneficial to support the ultimate detection of the development of a hole in the monitored segment and the determination of the direction relative to the site station in which the leak has occurred, as explained below.

The present invention can be used to detect the development of a pipeline break, its location on the segment to within several meters of its actual position and an indication of the extent of the breach, as will be discussed below. As shown in FIG. 1, a pipeline break is indicated at 40. If this break occurs suddenly, for example, near the center of the segment being monitored, depending on the size of the breach, the additional area though which liquid can flow must necessarily result in a sudden drop in pressure. The low pressure wave 45, and its associated drop in liquid density, will now travel at approximately the speed of sound, i.e., $V_s$, from the breach, outward in both directions toward the segment's two monitoring site stations 20.

The rate at which the pressure wave front falls is dependent on how the breach occurred, but since pipelines are under some pressure, the gradient can be assumed to be in the millisecond range. However, as it travels down the pipeline, it is possible that this gradient will become less steep, to, for example, the order of magnitude of several to tens of milliseconds. This is still quite fast, generally much faster than the gradient associated with valve or pump operations.

As the pressure wave passes into the path of the sonic beams of the two paths PATH1 and PATH2, the sudden drop in pressure will cause a drop in liquid density at this location, with the resultant drop in $V_s$ Since $V_s$ is being measured at the rate of, for example, one millisecond, and there is no inertia in the detection principle, this change will be immediately measured by the site station 20 computer. A short time later, dependent on the distance L of separation between the two paths, the same wave will pass through the second path, resulting in a similar drop in measured $V_s$. The passage of the pressure gradient past the two paths will occur at the two site stations at respective times, depending upon the location of the leak from the respective site station.

Figure 2:
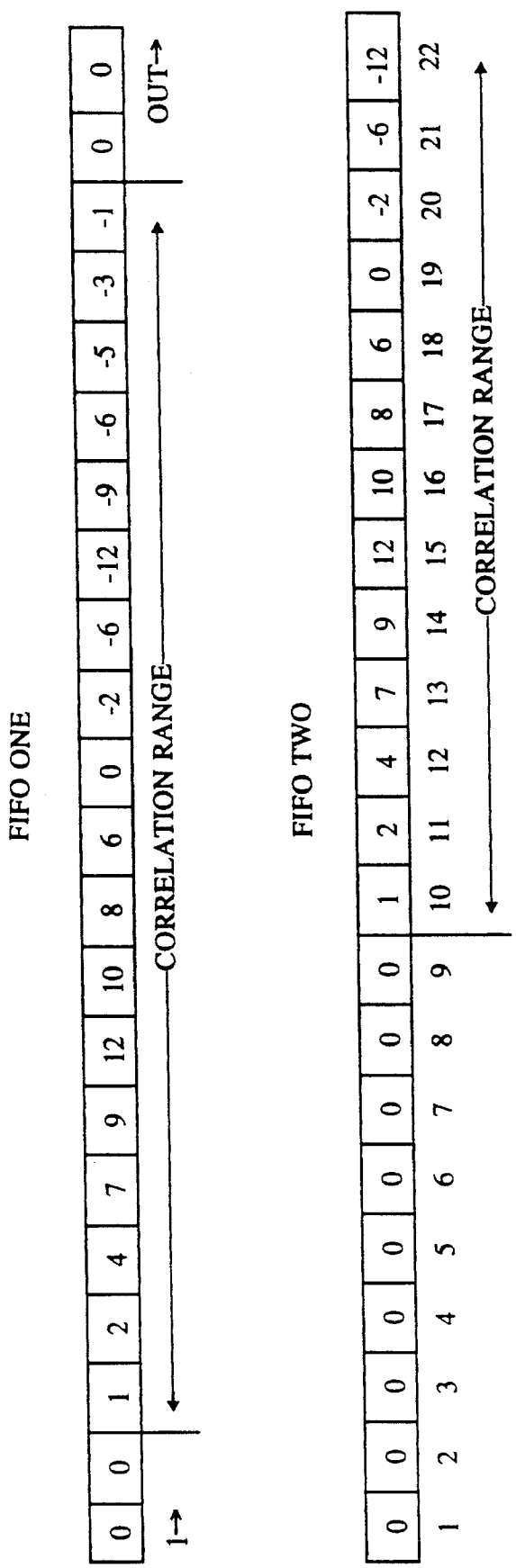
FIG. 2 shows two first in/first out (FIFO) memories which are employed in each site station showing how a correlation principle is employed at each site station of the present invention to determine the occurrence of a pressure change and the direction of the pressure change.

Now, it is well known that instruments like the Controlotron system 990 and system 1010 can measure $V_s$ to a resolution of nanoseconds, even in a single sonic pulse interrogation cycle. This corresponds to the effect on $V_s$ of a minor hole in a high-pressure pipeline. According to the invention, each millisecond, the current measurement of $V_s$ is subtracted from the prior measurement, so that the result is a measure of the change in $V_s$ ($\Delta V_s$) and likewise change in pressure as the wave-front passes through the sonic beam path. This difference measurement ($\Delta V_s$) can be stored in a FIFO (first in/first out) memory for each of the two paths supported by a single site station. These FIFOs for each path at each site station are shown in FIG. 2. The number of cells in the FIFO is selected to hold information for the duration of what is expected to be the time duration for an expected burst pressure wave transient due to a leak. Since each cell represents data for, in this case, one millisecond, a transient expected to take 30 milliseconds to decay will require a FIFO of 30 cells. In FIG. 2, 22 cells of exemplary FIFOs for each path of a site station are shown, although the FIFO can have more or fewer cells, depending upon the design, including, e.g., the size and type of pipeline.

The pressure wave which passes the second path in time will be identical to the first, if the distance L between them is short. Thus, the values of $\Delta V_s$ entered into the second FIFO are identical to the first, except they are displaced in time as shown, e.g. in FIG. 2. The direction of the pressure wave, i.e., its origin to the left or right of the site station, can be determined by the direction of the cell shift. By correlating the values of $\Delta V_s$ in the cells of each FIFO, displaced by a number of cells dependent on the time needed for the pressure wave to pass between the two sonic paths, pressure waves can be detected which originate from a direction dependent on the direction of the displacement of the cells in the two memories. Thus, displacement in one direction will enable correlation of pressure waves passing upstream while displacement in the opposite direction will enable correlation of waves passing downstream. In the exemplary illustration in FIG. 2, assuming fluid is flowing from left to right in the pipeline of FIG. 1, a pressure leak originating upstream has been determined in site station two because the pressure waveform determined by the stored $\Delta V_s$ differences in FIFO 2 are shifted by a number of cells toward the output side of the FIFO as compared with FIFO 1.

Slowly varying pressure waves, or slowly varying $V_s$ due to liquid temperature variation, changes in the product in the pipeline or due to pumps being turned on or off will be so slow as to cause only negligible $V_s$ changes at the rate required to exist in the FIFO at any given time, since a FIFO only holds, as shown in FIG. 2, 30 milliseconds or so of transient data at one time. In short, the correlation in a given direction will show only data associated with the fast transient of the type caused only by a pipeline breach if the number of cells in the FIFOs and the time period between $V_s$ samples is properly selected.

Thus, FIFO 1 is compared to FIFO 2 for a correlation between the two FIFOs. The amount of cell shift between the correlating values in the two FIFOs determines the direction of the transient, i.e., whether it is coming from upstream or downstream. Since this is done at both site stations on either side of a segment, the segment with the leak should have one site station determining an upstream disturbance and the other determining a downstream disturbance. Based upon these data, the device of the invention then determines a correlation factor CF to determine if the disturbance is a leak or some other condition.

The correlation factor CF basically determines the strength and arrival time of the transient, as will be described below. The strength of the transient and its arrival time determine whether the disturbance is likely a leak or some other condition, for example, the turning on of a pump or change in temperature, etc. Based upon the time of arrival of the transient at the two site stations, the master station 50, which polls the two site stations periodically with a signal 55, receives a $\Delta T$ signal which determines the time of arrival. Based on the $\Delta T$ signals from the two site stations, the exact location of the disruption can be determined by well-known triangulation techniques.

The system of the invention must be able to distinguish, however, between a perfect correlation due to a leak and a perfect correlation due to null FIFOs, i.e., FIFOs containing all zeros and which are consistent with no disruption. It is clear that perfect correlation will show a zero difference between the two FIFOs and that this is also the result that will be obtained from null FIFOs, i.e., FIFOs in which no transient is registered at all (because there is no difference in $V_s$ if no transient has occurred). It is thus necessary to differentiate between these two conditions, i.e., null FIFOs and perfect correlation due to a transient. This is done by recognizing that the integrated value of the $V_s$ differences in the FIFO is a measure of the strength of a transient. Therefore, to avoid the false correlation caused by null FIFOs, a correlation factor or strength factor CF is used in a detection algorithm, as shown below:

$$(CF) = FIFO \text{ sum}/(\text{displaced } FIFO \text{ difference} + X).$$

In this equation, the "displaced FIFO difference" is the difference between the sums of the correlated $V_s$ values in each FIFO. The "FIFO sum" is the sum of the correlated $V_s$ values for either FIFO. The term X is a small fixed number, intended to prevent the denominator from going to zero for the case of either null FIFOs or perfect non-zero correlation.

Each site station operates so as to store the maximum correlation factor (CF) which occurs between the time that the site station is interrogated by a master station and caused to send this value to it. Along with the value of CF, the site station transmits the exact number of milliseconds after the internal clocks of all site stations were last synchronized. Such synchronization occurs at every polling command, which is typically sent once per minute.

Alternating, the individual correlation factors can be transmitted to a remote master station which will perform correlation analysis.

The master station 50 has the ability to determine the exact time that a segment originated density wave pulse arrived at each segment site station. The Controlotron Model 990LD master station also has a complete picture of the liquids which are in each section of the pipeline, the current position of each different batch in the pipeline and the exact average $V_s$ of each batch at the current computed liquid temperature profile.

Accordingly, the master station 50 can compute the actual triangulated location of the actual source of the pressure disturbance, i.e., the source of the leak. This is done by known triangulation principles. Basically, the master station knows the time difference between when the transient pulse is received by each of the site stations. Based upon a knowledge of the liquid or liquids in the pipeline segment, the respective boundaries of each of the liquids (if applicable) in the pipeline segment, the average $V_s$ of the liquid or liquids in the segment of the pipeline, as well as the difference between the arrival of the pressure waveforms at each of the site stations, the distance to the disruption, i.e., the leak from each adjacent site station can be determined.

Since the resolution of the described system is of the order of magnitude of one millisecond and the speed of sound is around one meter per millisecond for hydrocarbon liquids, the theoretical resolution for leak location determination is about one meter. Naturally, this is far more precise than is actually needed for a fast determination of the actual leak site.

It is also clear that the strength or correlation factor CF is related to the size of the breach in the pipeline wall and data of this type will also be transmitted to the master station to provide an indication of the urgency of the pipeline break.

Figure 3:
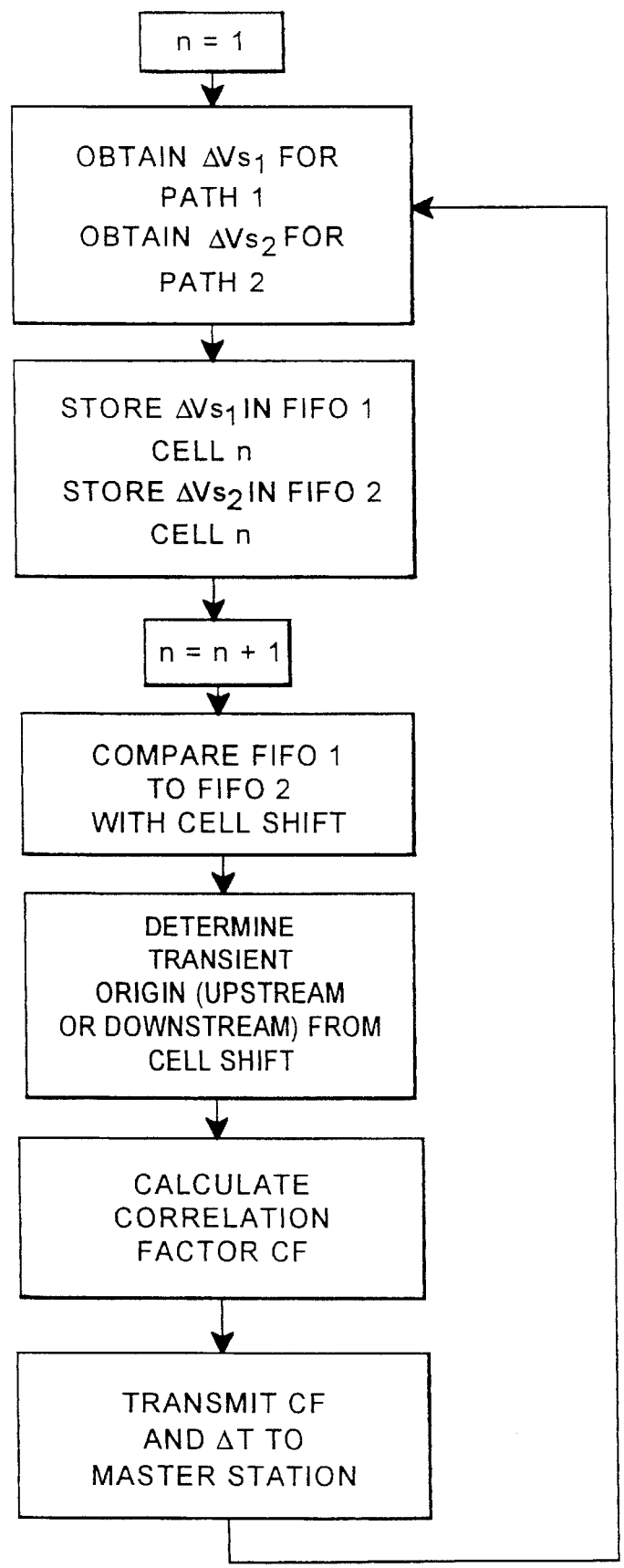
FIG. 3 is a flow chart showing how the site station determines a correlation factor which is useful in determining if a leak has occurred in a segment identified with the site station.
Figure 4:
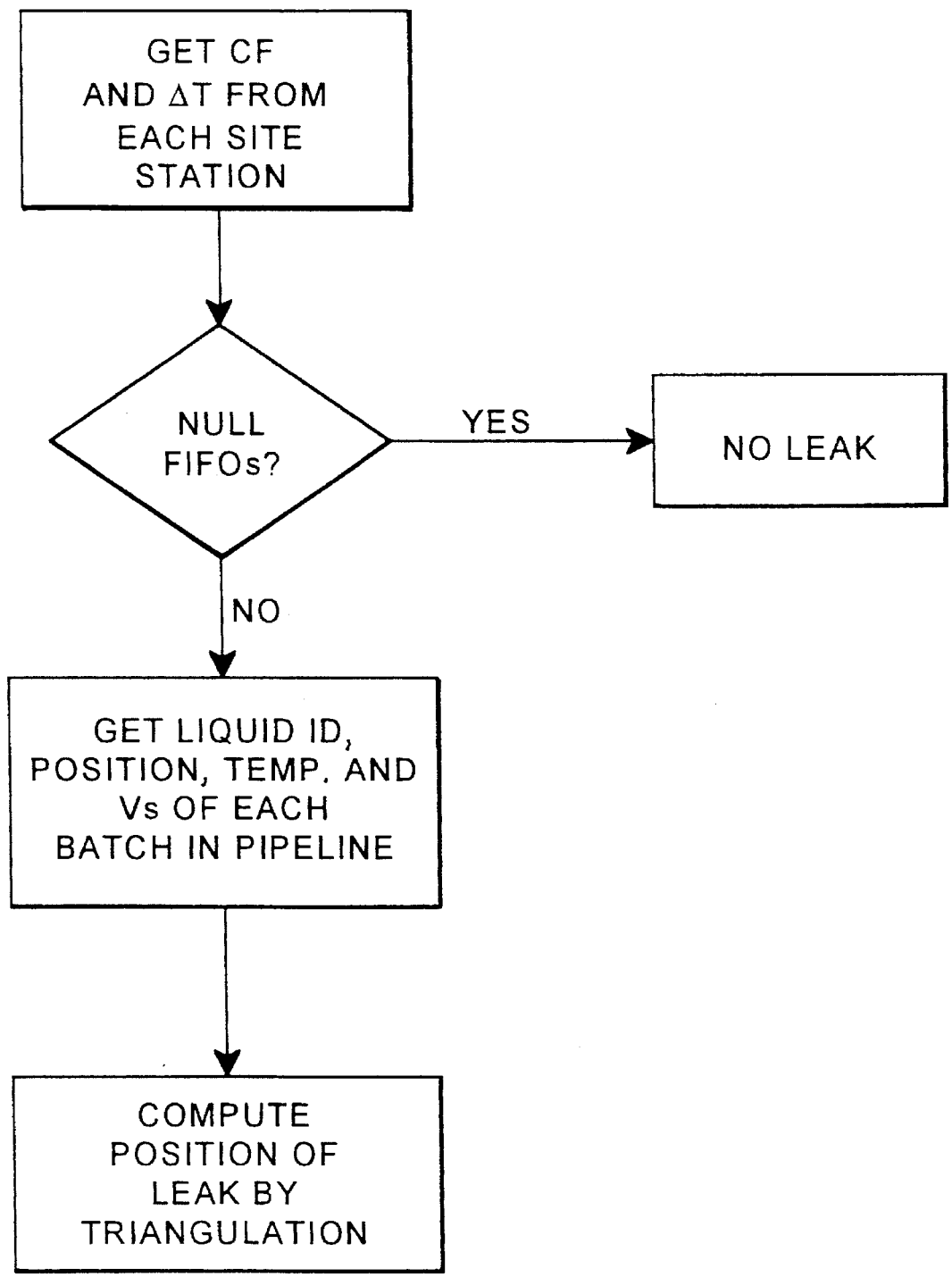
FIG. 4 is a flow chart implemented in the master station which determines the occurrence of a leak, based on parameters transmitted from the site stations, and if there is a leak, the position of the leak.

FIGS. 3 and 4 show flow charts for the software implementing the above described method and for determining the correlation factor CF and if there is a leak, in accordance with the discussion above.

It is clear that a network of this type for leak location detection can be installed, with one site station at either end of each pipeline segment. This system may be independent, with an associated master station and communication network.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A method for detecting the presence of a leak in a segment of a pipeline comprising:

providing site stations comprising an ultrasonic transducer assembly at the beginning and end of the pipeline segment, each said assembly having two pairs of ultrasonic transducers for determining the sonic propagation velocity $V_s$ of ultrasonic energy emitted by the transducers through fluid in the pipeline, each pair of ultrasonic transducers being displaced along the pipeline by a preset distance and each defining an ultrasonic energy flow path;

determining the value of $V_s$ for each ultrasonic energy flow path through the fluid in the pipeline at each site station at predetermined time intervals;

forming values $\Delta V_s$ defined as the difference between sequential values of $V_s$ at said predetermined time intervals for each flow path at each site station;

storing said $\Delta V_s$ values for each flow path in a memory having a predetermined number of memory cells, where a value of $\Delta V_s$ is stored in each cell;

determining if there is a correlation in the stored values of $\Delta V_s$ for each flow path;

discriminating, if there is a correlation between the $\Delta V_s$ values for each path, between a correlation caused by zero values of $\Delta V_s$ stored in the memory for each path and a correlation of $\Delta V_s$ values reflecting that a transient in the fluid in the pipeline has arrived at each site station; and determining, if there is a correlation wherein the $\Delta V_s$ values reflect that a transient has arrived at each site station, whether the correlation corresponds to a leak in the segment, and if so, indicating that a leak has occurred.

2. The method recited in claim 1, further comprising determining the location of the leak in the segment by triangulation of the transient arrival time between the two site stations at the two ends of the pipeline segment.

3. The method recited in claim 1, further comprising selecting the number of cells in the memory such that substantially all $\Delta V_s$ values from a transient caused by a leak will be stored in the memory, and substantially all $\Delta V_s$ values from a transient not caused by a leak will not be stored in the memory because such a transient not resulting from a leak is too slow to result in substantially all the $\Delta V_s$ values being stored in the memory.

4. The method recited in claim 1, where the step of discriminating comprises generating a correlation factor which indicates the relative strength and arrival time of a transient pulse as reflected in the $\Delta V_s$ values for each path in the memory, and using said correlation factor to determine whether there is a leak in the pipeline or some other condition which is not a leak.

5. The method recited in claim 4, wherein the step of storing comprises storing said $\Delta V_s$ values in a FIFO memory for each flow path.

6. The method recited in claim 5, wherein the step of storing in a FIFO memory for each flow path comprises storing in a shift register.

7. The method recited in claim 5, further comprising providing a number of cells in each FIFO memory sufficient to allow correlation of $\Delta V_s$ values in each FIFO memory for a transient arising from a leak in the pipeline and substantially preventing correlation of $\Delta V_s$ value in each FIFO memory for a transient arising from a condition in the pipeline that is not a leak.

8. The method recited in claim 5, further comprising determining the direction of a transient pulse in the fluid in the pipeline from the direction of a cell shift of correlating values in each of the FIFO memories.

9. The method recited in claim 8, wherein the step of generating the correlation factor comprises forming the following value CF:

$$CF = FIFO \text{ sum}/(\text{Displaced } FIFO \text{ Difference} + X)$$

where FIFO sum=the sum of all correlated values for either FIFO;

Displaced FIFO Difference=the difference between the sums of the correlated values for each FIFO; and X=a small fixed number to prevent a zero denominator.

10. Apparatus for detecting the presence of a leak in a segment of a pipeline comprising:

two site stations each having an ultra-sonic transducer assembly provided respectively at the beginning and end of the pipeline segment, each said assembly having two pairs of ultrasonic transducers for determining the sonic propagation velocity $V_s$ of ultrasonic energy emitted by the transducers through fluid in the pipeline, each pair of ultrasonic transducers being displaced along the pipeline by a preset distance and each defining an ultrasonic energy flow path;

a computer for determining the value of $V_s$ for each ultrasonic energy flow path through the fluid in the pipeline at each site station at predetermined time intervals, the computer further forming values $\Delta V_s$ defined as the difference between sequential values of $V_s$ at said predetermined time intervals for each flow path at each site station;

a memory wherein said $\Delta V_s$ values are stored for each flow path having a predetermined number of memory cells, where a value of $\Delta V_s$ is stored in each cell;

the computer further determining if there is a correlation in the stored values of $\Delta V_s$ for each flow path and discriminating, if there is a correlation between the $\Delta V_s$ values for each path, between a correlation caused by zero values of $\Delta V_s$ stored in the memory for each path and a correlation of $\Delta V_s$ values reflecting that a transient in the fluid in the pipeline has arrived at each site station; and the computer further determining, if there is a correlation wherein the $\Delta V_s$ values reflect that a transient has arrived at each site station, whether the correlation corresponds to a leak in the segment, and if so, indicating that a leak has occurred.

11. The apparatus recited in claim 10, wherein the computer further determines the location of the leak in the segment by triangulation of the transient arrival time between the two site stations at the two ends of the pipeline segment.

12. The apparatus recited in claim 10, wherein the number of cells in the memory is such that substantially all $\Delta V_s$ values from a transient caused by a leak will be stored in the memory, and substantially all $\Delta V_s$ values from a transient not caused by a leak will not be stored in the memory because such a transient not resulting from a leak is too slow to result in substantially all the $\Delta V_s$ values being stored in the memory.

13. The apparatus recited in claim 10, wherein the computer generates a correlation factor which indicates the relative strength and arrival time of a transient pulse as reflected in the $\Delta V_s$ values for each path in the memory, said correlation factor determining whether there is a leak in the pipeline or some other condition which is not a leak.

14. The apparatus recited in claim 13, wherein the memory comprises a FIFO memory for storing said $\Delta V_s$ values for each flow path.

15. The apparatus recited in claim 14, wherein the FIFO memory for each flow path comprises a shift register.

16. The apparatus recited in claim 14, wherein a number of cells in each FIFO memory is sufficient to allow correlation of $\Delta V_s$ values in each FIFO memory for a transient arising from a leak in the pipeline and substantially preventing correlation of $\Delta V_s$ values in each FIFO memory for a transient arising from a condition in the pipeline that is not a leak.

17. The apparatus recited in claim 14, wherein the computer further determines the direction of a transient pulse in the fluid in the pipeline from the direction of a cell shift of correlating values in each of the FIFO memories.

18. The apparatus recited in claim 17, wherein the means for generating the correlation factor comprises forming the following value CF:

$$CF = FIFO \text{ sum}/(Displaced\ FIFO\ \text{Difference} + X)$$

where FIFO sum=the sum of all correlated values for either FIFO;

Displaced FIFO Difference=the difference between the sums of the correlated values for each FIFO; and X=a small fixed number to prevent a zero denominator.

19. Apparatus for detecting the presence of a leak in a segment of a pipeline comprising:

two site stations each having an ultra-sonic transducer assembly provided respectively at the beginning and end of the pipeline segment, each said assembly having two pairs of ultrasonic transducers for determining the sonic propagation velocity $V_s$ of ultrasonic energy emitted by the transducers through fluid in the pipeline, each pair of ultrasonic transducers being displaced along the pipeline by a preset distance and each defining an ultrasonic energy flow path;

means for determining the value of $V_s$ for each ultrasonic energy flow path through the fluid in the pipeline at each site station at predetermined time intervals;

means for forming values $\Delta V_s$ defined as the difference between sequential values of $V_s$ at said predetermined time intervals for each flow path at each site station;

a memory for storing said $\Delta V_s$ values for each flow path having a predetermined number of memory cells, where a value of $\Delta V_s$ is stored in each cell;

means for determining if there is a correlation in the stored values of $\Delta V_s$ for each flow path;

means for discriminating, if there is a correlation between the $\Delta V_s$ values for each path, between a correlation caused by zero values of $\Delta V_s$ stored in the memory for each path and a correlation of $\Delta V_s$ values reflecting that a transient in the fluid in the pipeline has arrived at each site station; and means for determining, if there is a correlation wherein the $\Delta V_s$ values reflect that a transient has arrived at each site station, whether the correlation corresponds to a leak in the segment, and if so, indicating that a leak has occurred.

20. The apparatus recited in claim 19, further comprising means for determining the location of the leak in the segment by triangulation between the two site stations at the two ends of the pipeline segment.

21. The apparatus recited in claim 19, wherein the number of cells in the memory is such that substantially all $\Delta V_s$ values from a transient caused by a leak will be stored in the memory, and substantially all $\Delta V_s$ values from a transient not caused by a leak will not be stored in the memory because such a transient not resulting from a leak is too slow to result in substantially all the $\Delta V_s$ values being stored in the memory.

22. The apparatus recited in claim 19, wherein the means for discriminating comprises means for generating a correlation factor which indicates the relative strength of a transient pulse as reflected in the $\Delta V_s$ values for each path in the memory, said correlation factor determining whether there is a leak in the pipeline or some other condition which is not a leak.

23. The apparatus recited in claim 22, wherein the memory comprises a FIFO memory for storing said $\Delta V_s$ values for each flow path.

24. The apparatus recited in claim 23, wherein the FIFO memory for each flow path comprises a shift register.

25. The apparatus recited in claim 23, wherein a number of cells in each FIFO memory is sufficient to allow correlation of $\Delta V_s$ values in each FIFO memory for a transient arising from a leak in the pipeline and substantially preventing correlation of $\Delta V_s$ values in each FIFO memory for a transient arising from a condition in the pipeline that is not a leak.

26. The apparatus recited in claim 23, further comprising means for determining the direction of a transient pulse in the fluid in the pipeline from the direction of a cell shift of correlating values in each of the FIFO memories.

27. The apparatus recited in claim 26, wherein the means for generating the correlation factor comprises forming the following value CF:

$$CF = FIFO \text{ sum}/(Displaced\ FIFO\ \text{Difference} + X)$$

where FIFO sum=the sum of all correlated values for either FIFO;

Displaced FIFO Difference=the difference between the sums of the correlated values for each FIFO; and X=a small fixed number to prevent a zero denominator.

\* \* \* \* \*